US007107824B1

(12) United States Patent
Shiff et al.

(10) Patent No.: US 7,107,824 B1
(45) Date of Patent: Sep. 19, 2006

(54) APPARATUS FOR THE SEPARATION OF CYSTIC PARASITE FORMS FROM WATER

(75) Inventors: Clive J. Shiff, Baltimore, MD (US); Thaddeus K. Graczyk, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 683 days.

(21) Appl. No.: 09/006,999

(22) Filed: Jan. 14, 1998

(51) Int. Cl.
G01N 35/00 (2006.01)
(52) U.S. Cl. .................................... 73/61.43
(58) Field of Classification Search ............... 73/61.43; 209/3, 17; 210/745, 232, 360.1, 361, 781; 435/4, 34, 29, 41; 422/72; 494/36
See application file for complete search history.

(56) References Cited

U.S. PATENT DOCUMENTS

| 3,583,627 | A | * | 6/1971 | Wilson .................. 494/36 |
| 3,928,139 | A | * | 12/1975 | Dorn ................... 435/34 |
| 4,081,356 | A |   | 3/1978 | Zierdt |
| 4,212,948 | A | * | 7/1980 | Dorn ................ 435/288.1 |
| 4,675,110 | A |   | 6/1987 | Fay |
| 5,019,497 | A | * | 5/1991 | Olsson ............... 435/7.23 |
| 5,288,415 | A | * | 2/1994 | Chen-Wu et al. ........ 210/781 |
| 5,556,544 | A |   | 9/1996 | Didier |
| 5,846,439 | A | * | 12/1998 | Borchardt et al. ........ 210/781 |
| 5,866,071 | A | * | 2/1999 | Leu ..................... 422/72 |
| 6,020,150 | A | * | 2/2000 | Contant-Pussard et al. ... 435/34 |

FOREIGN PATENT DOCUMENTS

| CA | 871263 | 5/1971 |
| RU | 2011367 | 4/1994 |
| WO | WO 96/29427 | * 9/1996 |

OTHER PUBLICATIONS

California Lutheran University's Enriched Science Program, Module 2: Gel Filtration http://chemweb.calpoly.edu/chem/rice/csuperb/CLUES%20protocols/TWO/Lab2VerA.doc Revision date Jul. 1994, pp. 1-7 and link to the document from http://www.google.com.*
Whitmore et al., "Comparison of Methods for Recovery of Cryptosporidium From Water", Wat. Sci. Tech, vol. 27, No. 3-4, pp. 69-76, no month.*
http://www.sigmaaldrich.com Results of Oct. 31, 2002 searches for "dextran" and "sephadex", 4 pages.*
http://www.ionexchanger.com/Pharmaceuticals/xad.htm Printed Oct. 31, 2002, p. 1.*

(Continued)

*Primary Examiner*—Michael Cygan
(74) *Attorney, Agent, or Firm*—Ann S. Hobbs; Venable LLP

(57) ABSTRACT

A continuous flow centrifuge adapted with an insert of glass beads, sand or the like is used to concentrate cysts of microorganisms such as *giardia* or *cryptosporidium* from large volumes of water. The apparatus and methods are useful for the detection of contaminating microorganisms in groundwater and public drinking water.

8 Claims, 1 Drawing Sheet

OTHER PUBLICATIONS

Mudambi et al. "Mirex in Osweg River and Lake Ontario Water Columns", Proceed. 26th Conf. Great Lakes Res., May 1983, p. 32.*

Merriam-Webster's Collegiate Dictionary, 10th edition, 1998, no month, pp. 435, 436, and 847.*

Allcock et al. "Contemporary Polymer Chemistry", 1990, no month, Prentice-Hall, pp. 394-397.*

Shafer, M. M. "Biogeochemistry and Cycling of Water Column Perticulates in Southern Lake Michigan", thesis dissertation, University of Wisconsin-Madison, Jun. 1989, pp. ii, 14, and 17-20.*

Yousif et al. "Filtration, Centrifugation, and Mouse Exposure for the Detection of *Schistosome cercariae* in Water", J. Egypt. Soc. Parasitol., vol. 26, Apr. 1996, pp. 249-260.*

Barrett et al., A Continuous Flow Centrifuge for Testing the Presence of *Bilharzia cercariae* in Water, Central African Journal of Medicine, vol. 11, No. 11, Nov. 1965, pp. 338-340.

Bates et al., Collection of Suspended Particulate Matter for Hydrocarbon Analyses: Continuous Flow Centrifugation vs. Filtration, Estuarine, Coastal and Shelf Science (1983), 16, 107-112.

* cited by examiner

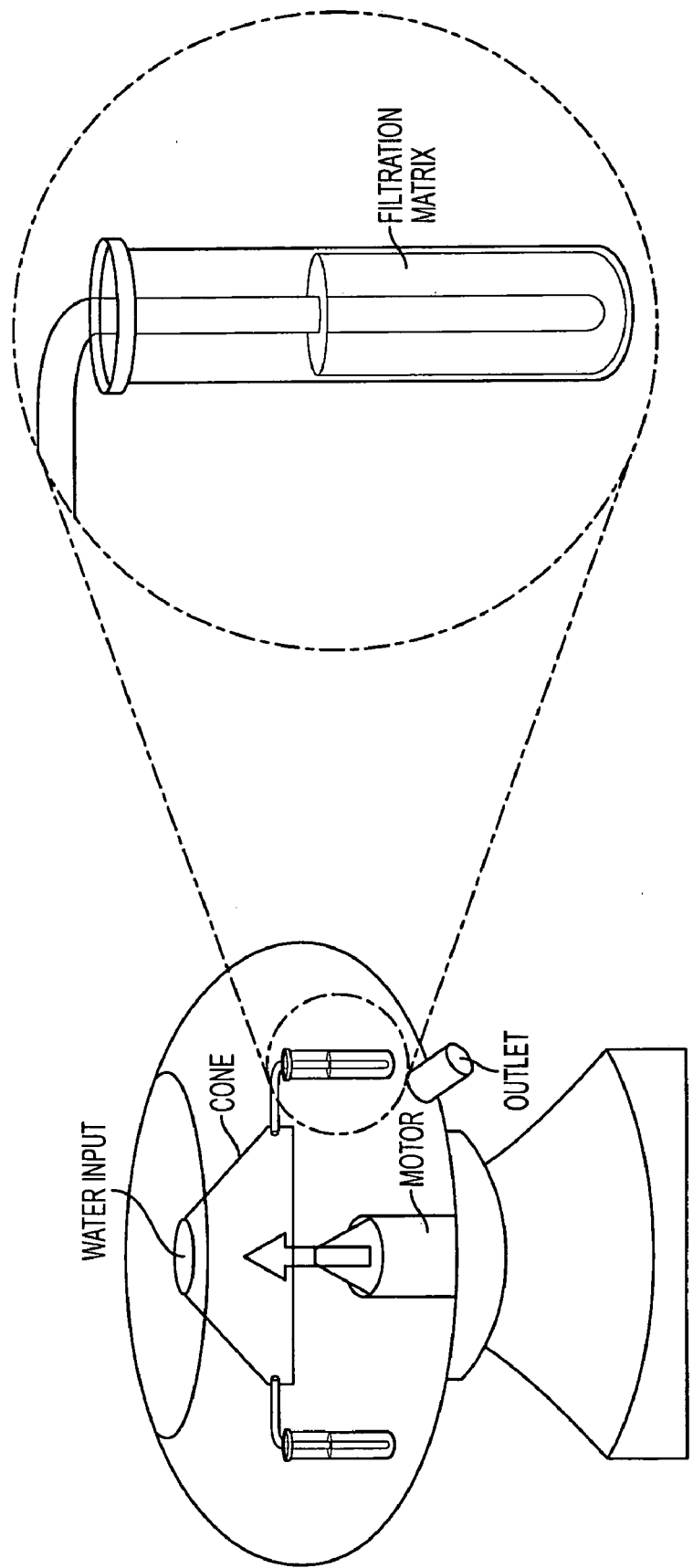

APPARATUS FOR THE SEPARATION OF CYSTIC PARASITE FORMS FROM WATER

BACKGROUND OF THE INVENTION

1. Field of the Invention

The invention is related to a continuous centrifugation apparatus and method. A continuous flow centrifuge adapted with an insert of glass beads, sand or the like is used to concentrate cysts of microorganisms such as giardia or cryptosporidium from large volumes of water. The apparatus and methods of the invention facilitate the detection of such contaminating organisms in groundwater and public drinking water.

2. Background Information

The problem of human cryptosporidiosis is emerging as one of the more serious issues confronting water purification and distribution facilities both in the United States and elsewhere. Recent outbreaks in Carrolton (Hayes et al., *N. Engl. J. Med.* 320:1372–1373, 1988), Jackson County, (Leland et al., *J. Am. Water Works Assoc.* 85:34, 1993) and Milwaukee (Mackenzie et al., 1994 *N. Engl. J. Med.* 331: 161, 1994), have brought matters to a head and in a recent announcement, the US Environmental Protection Agency has required testing of water supplies for oocysts of *Cryptosporidium parvum* to prevent transmission of the parasite.

Oocysts of *C. parvum* are common contaminants of natural waterways and have been found in surveys (Ongerth and Stibbs, *Appl. Environ. Microbiol.* 53:672–676, 1987); Hansen and Ongerth, *Appl. Environ. Microbiol.* 57:2790–2795, 1991). Outbreaks of cryptosporidiosis appear to be associated with technical aberrations at water treatment facilities or changes in river flow following drought conditions or high level of snow melt. Such conditions may combine to increase the load of *C. parvum* oocysts in the natural waterways, as well as allow the organisms to break through the filtration purification barrier and get access to human populations. The extent to which the organism occurs naturally has been explained recently in a review by Lisle and Rose (*Aqua* 44:103–117, 1995) and stresses the gravity of the public health problem.

Isolation and extraction of the oocysts of this parasite from natural water or from water being processed or from finished drinking water is difficult and expensive. Current methods utilize filtration as the main extraction process, but filtration of large volumes of water poses major problems particularly with natural water. Even at low turbidities (NTU values ±5), debris and colloidal material soon blocks the filtration medium making the procedure cumbersome and recovery rates become variable and unpredictable. To overcome this, filtration apparatus become large and require vacuum or pump assistance in order to process the samples. The regular method for the concentration and isolation of protozoal cysts from water utilize spiral wound filters to handle large volumes of water (Proposal P229, Annual Book of the American Society for Testing and Materials, Philadelphia, Pa.). The device requires a pump assisted, pressurized apparatus to extract material from the water sample. The apparatus is recommended for use in clarified water (turbidity ±1 NTU). Filtration of 380 L of water constitutes the sample. Following this the fiber filter unit is removed, the apparatus and filter rinsed with elution fluid, and the filter then slit into shreds with a razor knife, washed, kneaded and finally sonicated in 1 L volumes of elution fluid. The cysts which have been recovered from the water are then removed by elution and concentrated by centrifugation and purified on a Percoll-sucrose gradient. The procedure is cumbersome and leaves several procedures vulnerable to loss of material and hence a source of variability in the results. Reported concentrations of both *C. parvum* oocysts and *Giardia intestinalis* cysts from water samples analyzed through current methods have wide confidence limits due to poor and inconsistent recovery (5–40%), a high degree of variability (0–130%) and occurrence of false positives (AWWA: 1996 RFP No 364 "New Approaches for isolation of *Crytosporidium* and *Giardia*").

Use of centrifugation for retrieval of particulate matter from water is well known. However the concept of continuous flow centrifugation has not been used frequently apart from separation of cream from milk. The process differs from previously known continuous flow centrifugation methods in that a column of particulate matter is added to the fluid stream. The matrix (water) containing cysts is added continuously to the centrifuge, and excess water overflows and drains away, while the particles of interest remain trapped in the centrifuge tubes by force of gravity. A system was developed in Zimbabwe by Barrett and Ellison (*Cent. Afr. J. Med.* 11(11) 338–340, 1965) to separate trematode cercariae from natural waters. The present invention represents a significant advance over the system of Barrett and Ellison.

Extensive field testing demonstrates its superiority compared, for example, with filtration methods and used with considerable success in natural water systems in Egypt (Yousif et al., 1996). The unique operational advantage of this system is that it can handle large volumes of water irrespective of turbidity. It has been shown by Yousif et al., (1996) to operate both in clear water and water with turbidity above 30 NTU and concentrate particulates in the centrifuge tubes even at speeds of 2–3,000 rpm. The cystic stages of both *C. parvum* and *G. intestinalis* are much smaller than the trematode larvae and other particles which were isolated by the centrifuge described by Barrett and Ellison, so additional modifications were needed to proceed.

SUMMARY OF THE INVENTION

It is an object of the invention to provide an apparatus and method for the separation of cystic parasite forms from natural and clarified water. The features of the invention overcome problems associated with other methods which have been used or contemplated for this purpose, for example the problem of clogging which is associated with filtration methods. Thus, the invention will be suitable for separating and detecting contaminating microorganisms such as parasite cysts or waterborne bacteria such as fecal coliforms.

These and other objects are achieved by the use of a novel method for extraction and isolation of these important microorganisms such as *Cryptosporidium* and *Giardia intestinalis* as well as fecal coliforms from natural water in volumes which are realistic to detect these stages and are yet practical to handle. The method is inexpensive and designed to have a field or sample collection component and a laboratory or analytical component. The apparatus has been developed as a prototype and demonstrated to be effective with the oocysts of *C. parvum*.

The apparatus of the invention is centrifuge which is designed to accept a continuous stream of water containing particulate matter through a central hollow cone while the centrifuge is spinning. The water is transferred from the cone to the base of two or more (required for balance) centrifuge tubes via flexible rubber tubing connected to outlets on the lateral margin of the cone. Each tube contains a filtration matrix (glass sand), which functions as a filtration column. This filtration column is held in place by centrifugal force which also drives the water to the base of the tube, then back up through the filtration column. The water overflows from the tubes and is discarded through a venting port in the centrifuge shroud. It is the concept and design of a filtration column held in situ by centrifugal force and which operates from the base upwards that is unique and distinguishes the apparatus from prior art. The use of glass sand of various diameters from 120 to 50 micrometers or fine sand 200–50 micrometers in the filtration column is also critical. The apparatus can process approximately 2 L water per min. which will conveniently enable the examination of samples of 100 L which is normally required for assessing loads of parasite cysts 2–4 micrometers in diameter in natural water of the type processed for drinking. It is expected that an apparatus which can process at least about 1.5 L/min will be useful for the methods of the invention. The apparatus can separate microorganisms of the same size order as *Cryptosporidium* oocysts (3–7 μm) from the water.

The microorganisms and any cystic material are then removed from the filtration matrix and measured or counted. Bacteria may be plated out on isolation media. Cysts may be removed by the use of elution fluid after the method of Aldom and Chagla (*Applied Microbiology* 20:186–187, 1995), which has an efficiency of 78%.

The term "Centrifuge tube", according to the invention, has the standard meaning known to persons of ordinary skill in the art, and includes any container or vessel of a shape and size to be operable in the invention and to hold a filtration column of sand or another matrix suitable for separating cysts according to the method of the invention. Such tubes will generally be cylindrical in shape and enclosed on the bottom. The tubes which are contemplated include, but are not limited to disposable tubes of glass, plastic or other suitable material, which have been specifically designed to fit an apparatus of the invention and are prefilled with matrix material, or reusable tubes which may be prefilled or filled with matrix material "on-site" by the operator. The tubes may attach directly to the rotor, or may be inserted into suitable holders or "buckets" for operation. In one preferred embodiment of the invention, "one use" disposable filtration columns which are manufactured to fit permanently attached or detachable centrifuge tubes are inserted into the tubes prior to each sample run.

Accordingly, the invention comprises a continuous flow centrifuge apparatus which is adapted to include a filtration column of particulate material. Thus, the invention is an improvement in a continuous flow centrifuge apparatus comprising the addition of a filtration column of particulate material. The particulate material is graded glass beads or sand of a size range which is suitable for trapping the microorganism(s) of particular interest. In general, particulate material with an size range of 120–50 μm in a column which is at least 7 cm in length will be most useful for these purposes. The invention is considered to be particularly useful for isolating and detecting the cysts of *cryptosporidium* or *giardia*.

In a particularly preferred embodiment, the particulate material is graded glass beads of 120–50 μm or fine sand of 200–50 μm in a column of at least about 7 cm in height.

The invention also includes a method for concentrating or isolating a microorganism from an aqueous suspension, said method comprising centrifuging said solution using the apparatus of the invention. Thus, the method of the invention is an improvement in a method for concentrating, isolating or detecting a microorganism using a continuous flow centrifuge, the improvement comprising using a filtration column of particulate material in the fluid stream of the centrifuge.

BRIEF DESCRIPTION OF THE DRAWINGS

FIG. 1: Continuous flow centrifuge apparatus. The water sample is introduced into the top of the cone and passes through outlets at the bottom edge of the cone, positioned adjacent to centrifuge tubes through flexible tubing which must fit securely over the outlet ports on the lateral margin of the cone. The flexible tubing extends to the bottom of the centrifuge tube so that as the centrifuge operates the liquid sample passes into the bottom of the centrifuge tube and rises through the filtration matrix to the top. The filtered sample then passes out of the top of the centrifuge tube as overflow, from whence it flows to the bottom of the containment vessel and is removed through a waste outlet. At the end of each run, the filtration matrices can be removed and tested for cysts, etc. as described hereinafter.

DETAILED DESCRIPTION OF THE INVENTION

An exemplary apparatus is shown in FIG. 1. This illustrative example is a standard bench top swinging bucket centrifuge (Clinical Model IEC 428) with 6-place horizontal rotor modified to accept a continuous flow of water through an internally machined brass hollow cone. This example operates efficiently at speeds of up to 5,000 rpm. Outlet ports from the cone match the positions of the 6 centrifuge tubes and are connected to the tubes via flexible tubing reaching to the base of each tube. Each centrifuge tube is designed to be filled with glass sand (Microlite) or some similar matrix which will be effectively a filtration column of graded glass beads.

Suitable filtration matrices include Superbrite Glass Beads made by 3M Reflective Products Division with particles sized 120 μm (90%) to 50 μm (10%) diameter (this material is referred to as glass beads or glass sand); filtration sand graded from 200 μm to 50 μm diameter in equal amounts (this is referred to as fine sand). Essentially, the matrix acts as a particle filter which is coarse enough to allow a flow of water containing clay or suspended colloidal material while still retaining small particles such as *C. parvum* oocysts. Other suitable materials for the filtration matrix will also be able to be determined by persons of ordinary skill in the art using routine experimentation.

The instrument maintains the integrity of the columns while the head is spinning. This can be achieved with the head spinning at 3–4,000 rpm.

The apparatus and method thus employ centrifugal force, not only to concentrate particles, but also to maintain the filtration columns (six in this case) composed of glass sand or a similar matrix in a packed form while spinning and which when suspended in liquid phase and spinning at approx 3–4,000 rpm establishes a filter column. Water containing the particulate matter is introduced into the spinning centrifuge through a central hollow cone, and is lead through flexible tubes to the base of each column (tube), rises through the column while spinning and overflows to waste. Thus, water is forced by gravity to the base of each spinning tube, rises through the column and flows to waste through the overflow duct.

When a sufficient sample has been centrifuged, the machine is stopped and each centrifuge tube emptied into a beaker containing eluting medium. After 60 min on a shaking bed the slurry is sedimented and the supernatant filtered through a millipore filter (1.2 μm) under vacuum. The filter is removed, dissolved in acetone, centrifuged at 650×g for 15 min in acetone, 95% ethanol, the 75% ethanol and finally eluting fluid. Then 10 μl aliquots will be placed in a hemacytometer for counting of oocysts following the technique of Aldom and Chagla (1995). These authors recovered oocysts from 360 L of spiked water and examining aliquots determined a recovery rate of 70.5% with a high level of reproducibility. The data shown in Table 1 demonstrate that this technique produces a very high level of recovery.

Tests using a prototype centrifuge demonstrate that the apparatus will deal with approximately 2 L per minute, centrifuging 25 L of moderately clear water (Baltimore, Md. tap water with some rust, diatoms and other particles) in 12–15 min. The filter medium was glass sand (microlite) 90% 120 μm: 10% 5 μm diameter. Microscopic examination of material released from the filter medium using elution fluid showed numerous flagellate and spiral forms of bacteria as well as spherical diatoms and plant pollen in the range 2–4 μm diameter.

Preliminary data show effective recovery of *C. parvum* oocysts from a 25 L sample of water spiked with 10,000 oocysts with a recovery of 78.2%. This is a high level of efficiency when compared with standard filtration methods which may approach 30% recovery (Nieminski et al., *Appl. Environ. Microbiol.* 61:1714–1719, 1995). This demonstrates that the oocysts will adhere to a column of glass beads and that they can be effectively recovered with greater efficiency than by using current technology.

Description and Operation

The sample of water (100 L) is placed in an overhead tank and connected to the centrifuge apparatus by tube via a stopcock. The centrifuge is loaded by adding 15 g of microlite glass sand to each tube ensuring that the central flexible pipe is not obstructed or kinked and that it reaches the base of the tube. The centrifuge is activated and when it reaches constant speed (approx. 4,000 rpm) the stopcock is opened to allow a flow of 1.5–2.0 L/min. directed into the central cone. Overflow is voided to drain. Centrifugation continues until the water is finished and the centrifuge turned off.

When the rotor is still, the tubes are removed and the contents flushed out into beakers using elution fluid (phosphate buffered saline with 0.1% Tween 80; SDS and 0.001% Sigma anti-foam; pH 7.4). Each beaker will contain 100 ml of eluent and slurry. The 6 beakers will be gently shaken for 60 min. at 4 C, then the glass sand allowed to sediment and the supernatant decanted with washing into a large beaker. All supernatants and washings from the 6 beakers will be combined and this fluid will be passed through a millipore filter (1.2 μm pore size) under vacuum. Following filtration of the sample, the filter membrane will be dissolved in 200 ml acetone, centrifuged (600×g) 2 min., resuspended and centrifuged sequentially in acetone, 95% ethanol and 70% ethanol and eluting fluid (10 ml). Aliquot parts of this concentrate which contains all particulate matter from the 100 1 sample are then examined using the Merifluor *Cryptosporidium/Giardia* test kit.

References cited herein are hereby incorporated by reference.

What is claimed is:

1. In a continuous flow centrifuge apparatus, the improvement comprising the addition of a filtration column of particulate material.

2. The apparatus of claim 1 in which said particulate material is graded glass beads or sand.

3. A method for concentrating or isolating a microorganism from an aqueous suspension, said method comprising centrifuging said suspension using the apparatus of claim 1.

4. In a method for concentrating, isolating or detecting a microorganism using a continuous flow centrifuge, the improvement comprising using a filtration column of particulate material in the fluid stream of the centrifuge.

5. The method of claim 4 in which the microorganism is a cyst of cryptosporidium or *giardia*.

6. In a continuous flow centrifuge apparatus, the improvement comprising the addition of a filtration column of particulate material, wherein said particulate material is selected from the group consisting of graded glass beads of 120–50 μm and fine sand of 200–50 μm and the column is at least about 7 cm in height.

7. A continuous flow centrifuge apparatus which includes a filtration column of particulate material having a size range of 120–50 μm.

8. In a method for concentrating, isolating or detecting a cyst of cryptosporidium or *giardia* using a continuous flow centrifuge, the improvement comprising using a filtration column of graded glass beads or sand in the fluid stream of the centrifuge.

* * * * *